United States Patent [19]

Burns

[11] 4,255,192

[45] Mar. 10, 1981

[54] HOMOGENOUS BONDING OF DISPERSED PHASE ALLOY

[75] Inventor: Charles F. Burns, Lansdowne, Pa.

[73] Assignee: Pennwalt Corporation, Philadelphia, Pa.

[21] Appl. No.: 103,887

[22] Filed: Dec. 17, 1979

Related U.S. Application Data

[63] Continuation-in-part of Ser. No. 34,091, Apr. 27, 1979, abandoned.

[51] Int. Cl.$^3$ ............................ C22C 5/06; C22C 7/00
[52] U.S. Cl. .................................... 75/169; 75/0.5 R; 75/134 C; 75/255; 134/3
[58] Field of Search ................. 75/0.5 R, 255, 173 R, 75/169, 134 C; 134/2, 3

[56] References Cited

U.S. PATENT DOCUMENTS

| | | | |
|---|---|---|---|
| 1,278,744 | 9/1918 | Poetschke | 134/25 A |
| 3,305,356 | 2/1967 | Youdelis | 75/134 T |
| 3,980,472 | 9/1976 | Asgar | 75/0.5 R |
| 4,039,329 | 8/1977 | Youdelis | 75/255 |
| 4,080,199 | 3/1978 | Sung | 75/0.5 R |

*Primary Examiner*—T. M. Tufariello
*Attorney, Agent, or Firm*—Robert G. Danehower

[57] ABSTRACT

Dispersed phase dental alloy made by mechanically blending mixtures of lathe cut dental amalgam alloy particles and spheroidal silver-copper alloy particles has superior properties as an amalgam when a mechanical blend of the mixture of alloy particles is treated prior to amalgamation with dilute aqueous mineral acid solutions or with methyl alcohol.

9 Claims, No Drawings

HOMOGENOUS BONDING OF DISPERSED PHASE ALLOY

BACKGROUND OF THE INVENTION

This application is a continuation-in-part application of U.S. Pat. No. 34,091 filed Apr. 27, 1979, abandoned.

The failure of dental restoration amalgam is believed due to the presence of excessive particles of weak Gamma II ($Sn_{7-8}Hg$) in the amalgam. A new metallurgical system was developed by Youdelis, U.S. Pat. No. 3,305,356 in 1967 in which the silver-copper eutectic alloy (72%Ag–28% Cu) was mechanically mixed with up to 60% weight of a conventional dental alloy before amalgamation. Improved compressive strength and flow characteristics were obtained by this procedure.

It was at first thought that the increase of the compressive strength of amalgams made from this alloy mixture was due to the dispersion hardening mechanism of the silver-copper phase. Subsequent investigation indicated that what actually occurred is a solid state diffusion reaction which includes a partial disassociation of the silver-copper phase after amalgamation with mercury. This silver-copper phase reacts with and eliminates a secondary phase called Gamma II ($Sn_{7-8}Hg$). Gamma II is the weak link in dental amalgam and its reduction or complete elimination is important in dental amalgam restorations.

Difficulties were encountered with the physical mixture of the two alloys used by Youdelis in that the silver-copper phase settles away from the conventional lathe cut alloy producing a non-homogenous mixture of lathe cut particles and silver-copper alloy spheres. Upon reaction with mercury, a non-uniform amalgam mixture was produced. The amalgam will vary from one dispensation of alloy to another. Moreover, the reduction and/or elimination of Gamma II is dependent on the close proximity of the silver-copper phase which reduces it after amalgamation and settling out of the silver-copper spheres from the alloy mixture minimizes the required intimate contact.

Two commercial manufacturers of dispersed phase alloy have overcome the settling out of the silver-copper eutectic spheres by melting the mixture of alloys and spheroidizing the molten mixture. However, this method nearly doubles the cost of manufacture compared to mechanically blending the mixed alloys.

SUMMARY OF THE INVENTION

I have now discovered that if lathe cut dental amalgam alloy particles and spheroidal silver-copper alloy particles are treated with the chemical treating solutions of my invention, the heavier silver-copper alloy particles will not settle out of the mechanical mixture of the two alloys.

My treating solutions are one or more mineral acids or methyl alcohol solution. The alloys are contacted with the treating solutions for a time sufficient to electrostatically bond or agglommerate the mixture of the alloy particles. When mineral acids are used, a mild etching of the surface of the alloys also takes place. After contact of the alloy particles with the treating solution, it is separated, the alloy particles are then washed with water and the particles are air-dried.

This treatment provides an alloy which will produce an amalgam restoration having superior physical properties with a low tendency to creep and a reduced tendency to fracture.

PRIOR ART

Poetschke in U.S. Pat. No. 1,278,744, describes a process in which he treats conventional lathe cut alloys with alcohol acidified with hydrochloric acid to remove surface oxidation and surface sulfidation. Poetschke found that his treatment process produced an alloy with a bright silvery appearance.

Young and Wilsdorf in Biomed Mater. Res. Vol. 6, PP. 88–103 (1972) investigated the effect of treating spheroidal particles of a conventional silver-tin alloy with a 5% aqueous hydrochloric acid solution. Young and Wilsdorf concluded that the tensile strength of silver-tin amalgams increased by about 40% when the alloy samples were prepared from the spherical silver-tin alloy particles after cleaning them in a 5% solution of hydrochloric acid in distilled water.

Young and Wilsdorf also observed that the fracture of tendered amalgam made from cleaned alloy particles has been shown to propagate by straight cracks which pass through the matrix intergranularly and alloy particles by cleavage. In amalgams made with the "as received" alloy, the fracture propagated around the alloy particles because of poor matrix particle bonding.

Youdelis in U.S. Pat. No. 3,305,356 discloses that Dental Amalgam Alloy can be improved by dispersing a hard alloy such as the silver-copper eutectic alloy throughout the amalgam.

It is also known as of the present time that manufacturers of the dental amalgam alloy, that is the silver-tin-copper-zinc alloy which is produced in comminuted form by lathe cutting is treated with dilute aqueous acid solution to remove tarnish and surface impurities in the manner disclosed by Poetschke.

DETAILED DESCRIPTION OF THE INVENTION

The solutions used to treat the alloy particles will be one of the following solutions: hydrochloric acid solution, 5 volume percent aqueous solution to 100 volume percent acid; sulfuric acid solution, 5 volume percent to 50 volume percent aqueous solution; nitric acid solution, 5 volume percent to 20 volume percent aqueous solution; methyl alcohol, 5 volume percent aqueous solution to 100 volume percent methyl alcohol. The preferred chemical treatment solutions are 10 volume percent aqueous hydrochloric acid solution, 5 volume percent aqueous sulfuric acid solution, 10 volume percent aqueous nitric acid solution and 10 volume percent methyl alcohol in water. By volume percent is meant volume percent of the concentrated acid or methyl alcohol in water. Concentrations lower than those given above may be used provided that the treating time is extended to allow for the lower concentration.

The alloy particles of the invention will be treated by bringing the alloy particles into contact with the treating solutions for a time sufficient to electrostatically bond or agglommerate the alloy particles which prevents the heavier silver-copper alloy spheres from separating from the mixture. This treating time will vary from about 5 to 30 minutes.

The amount of treating solution required to treat the mixture of alloys is an effective amount. An effective amount is that quantity required to thoroughly wet the mixture of alloys on a washing screen or the amount necessary to cover the mixture of alloys in a treating container. Generally, about 1.5 to 5 cc. of treating solution is used per/gram of alloy mixture and thus would also be an effective amount.

The treating solutions are brought into contact with the alloy particles in any convenient manner, e.g., the alloy particles may be placed in a vessel equipped with a stirrer and the treating solution added to the vessel. In another aspect of my invention, the treating solution may be brought into contact with the alloy particles by passing the treating solution through the alloy particles while they are retained on a screen in the manner taught by Poetschke, U.S. Pat. No. 1,278,744 which is incorporated herein by reference.

In the practice of my invention, the lathe cut dental amalgam alloy particles and the spheroidal silver-copper alloy particles are mechanically mixed in any suitable blending apparatus. Typical blending apparatus are conical blender and twin shell blender. The proportion of the spheroidal silver-copper alloy will vary from 20 to 50% by weight of the mixture of alloys. A preferred blend will contain about two-thirds of the dental amalgam alloy and one-third of the spheroidal silver-copper alloy particles. If the lathe cut alloy is separately treated with alcohol acidified with hydrochloric acid as described by Poetschke and the spheroidal silver-copper alloy separately washed with the treating solutions of my invention and then if the two alloys are mechanically blended, no significant increase in the one-hour strength of the amalgam restoration is obtained.

After treating the alloy particles with the treating solution for the required length of time, the treating solution is separated from the alloy particles by use of a filter screen, by decantation, by centrifuging or by any other convenient method of separating a liquid from a solid. The treated alloy particles are then washed with water, preferably demineralized water or distilled water, to remove all traces of the treating solution and finally air-dried. Any conventional washing and drying technique is satisfactory in the process of my invention. Washing with anhydrous methyl or ethyl alcohol may be used to assist the drying of the alloy mixture.

The dental alloy mixture bonded by the treatment process of my invention consists of a mechanical mixture of lathe cut silver-tin-copper-zinc dental amalgam alloy and silver-copper eutectic alloy. The term "dental amalgam alloy" as used throughout the specification and claims defines an alloy having the following composition: Silver 40 to 75%, tin 20 to 30%, copper 2 to 30% and from 0 to 30% of one or more of the metals selected from the group consisting of indium, zinc, gold, mercury, manganese, cadmium and aluminum. All percentages are by weight.

The preferred dental amalgam alloy which is lathe cut will have a composition of silver—69 to 72.5% weight, copper—1 to 3.5% weight, zinc—0.02 to 2.0% weight and the balance tin. A commercial lathe cut dental amalgam alloy which I frequently use has a composition of silver—70% weight, tin—25% weight, copper 3.5% weight and zinc 1.5% weight.

The lathe cut dental amalgam alloy described above will be comminuted by cutting particles from a bar on a lathe.

The particle size distribution will be controlled by using only particles through a 200 mesh Tyler screen. Preferably, the lathe cut particles will pass 325 or 400-mesh Tyler screen. The lathe cut particles may be reduced in size as required by grinding in a ball mill.

The spheroidal shaped particles of the silver-copper alloy of my invention will have a composition of silver—54 to 72% weight, copper—24 to 40% weight and varying amounts of nickel, zinc, tin and indium. Alloys coming within the above composition will be referred to as the "silver-copper phase alloy." The preferred silver-copper phase alloy is the eutectic 72% silver-28% copper alloy. The silver-copper phase alloy is used in spheroidal form. The preparation of silver-copper phase alloy in spheroidal form is described in Youdelis, U.S. Pat. No. 3,305,356 granted Feb. 21, 1967, which is incorporated herein by reference. The particle size of the silver-copper spheroids will be minus 325 mesh and preferably minus 400 mesh Tyler screen.

By treating the lathe cut alloy particles and the spheroidal silver-copper alloy with the treating solutions of my invention as described above, I have found that the mechanical mixtures of the two types of alloy will aglomerate or bond to each other and will not segregate during shipping and storage and will remain as a homogenous mixture until used by the dentist. The chemical treatment of this invention produces an electrostatic charge on the particles which attracts the spheroidal silver-copper alloy to aglommerate on the surface of the lathe cut particles and prevents the heavier silver-copper particles from settling out.

This homogenous mixture of alloys upon amalgamation provides for close proximity of the silver-copper alloy particles to the Gamma II Ag-Sn and enables the silver-copper to substantially reduce the proportion of Gamma II particles in the restoration by solid state diffusion.

The reduction of the Gamma II phase in the restoration leads to increased compressive strengths and decreased creep or flow properties which in turn lead to a reduction in fractures of the restorations. The practice of my invention provides the dentist with a high quality, high copper dispersed phase alloy at a cost only slightly above that of the conventional lathe cut alloy.

One of the most important benefits provided by the chemical treatment of the alloy particles in accordance with my invention was the increase in the one-hour compressive strengths of the alloy mixtures of this invention. The one-hour compressive strengths of an amalgam made from 66.6 parts by weight of untreated lathe cut dental amalgam alloy particles having a composition of silver—70%, tin—25%, copper—3.5% and zinc—1.5% with 33.3 parts by weight of untreated spheroidal alloy particles having a silver content of 72% and copper content of 28% was 13,000 and 16,000 pounds per square inch on two measurements, the average being 14,500 pounds per square inch.

In the same manner, 66.6 parts by weight of lathe cut dental amalgam alloy of the composition described above was treated with 5 volume percent sulfuric acid solution, followed by washing and drying, while 33.3 parts by weight of spheroidal silver-copper eutectic was treated in the same manner, and thereafter the two alloys were mixed by mechanical blending and then subjected to the one-hour compressive strength test. The compressive strength was 16,000 psi.

When an identical mechanical mixture of the two alloys described above was treated with five volume percent sulfuric acid solution, followed by washing and drying, the one-hour compressive strength was 34,500 pounds per square inch or an increase of 138%.

When the same alloy mixture described above was treated with 10 volume percent hydrochloric acid solution followed by washing and drying, the one-hour compressive strength was determined to be 31,500 pounds per square inch or an increase of 117%. The increase for the ten volume percent methyl alcohol solution was 64%.

The static creep of the two-thirds blend of lathe cut dental amalgam alloy and one-third (by weight) of the silver-copper eutectic spheres treated with 10% hydrochloric acid was 0.15%. See A. D. A. Specification No. 1 for procedure. This is a great improvement over S. S. White's conventional amalgam alloy sold under the trademark New True Dentalloy which showed a creep of 1.17%.

The best mode of practicing my invention will be observed by consideration of the following examples

EXAMPLE 1

Dental amalgam alloy of silver—70%, tin—25%, copper—3.5% and zinc 1.5% composition was comminuted by cutting on a lathe, then ground in a ball mill, and finally screened to obtain particles which passed through 325 mesh Tyler screen.

Silver-copper alloy was prepared in spheroidal form and screened through 400 mesh Tyler Screen.

The lathe cut dental amalgam alloy particles were mixed in a conical blender for approximately thirty minutes. The mixture of alloys was then annealed in an air oven at 100° C. for about 3 hours. After cooling, the mixture of alloys was placed in a container, the treating solution of my inventon was then added to the container and the mixture was stirred for about 5 to 30 minutes at ambient room temperature. When the treating was finished, the mixture of alloys was separated from the treating solution, for example, as by filtering on a screen. The mixed alloy particles were then washed with demineralized water until all trace of the treating solution was removed.

The mixute of alloys was then dired by hot air drying. The washed and dried mixture of the alloys was then made into cylindrical pellets in the manner specified in American Dental Association Specification No. 1, 1977 edition, section 4.3.3. The cylindrical pellets, 4 mm. in diameter and 8 mm. long, were then tested for compressive strength with an Instron Universal Testing Machine in the manner set forth in section 4.3.5 of the aforesaid specifications.

EXAMPLE 2

Following the procedure of Example 1, the ratio of silver-copper alloy spheres in a mechanical mixture with Dental Amalgam Alloy was varied between 20 and 50% by weight. The various mixutes were treated with 10% hydrochloric acid (10 Vol. Conc. HCl to 90 Vol. water) and thereafter the one-hour compressive strengths were determined. The working time is the time between trituration with mercury and the set time in the mold. The compressive strenths and working times are shown in Table 1.

TABLE I

Variation of Ag—Cu Eutectic in Lathe Cut Dental Amalgam Alloy
Treatment - 5 Minutes in 10% HCl

| Ag—Cu Eutectic | Lathe Cut Alloy[A] | Working Time | 1 Hr. Sc. |
|---|---|---|---|
| 20% | 80% | 3¾ min. | 19,200 psi. |
| 33⅓% | 66⅔% | 3½ min. | 31,750 psi. |
| 40% | 60% | 3¼ min. | 26,900 psi. |
| 50% | 50% | 1½ min. | — |

[A]Ag - 70%, Tin - 25%, Copper - 3.5% and Zinc - 1.5%

EXAMPLE 3

Following the procedure of Example 1, mixtures of dental amalgam alloy lathe cut particles having the composition shown in Table I and silver-copper eutectic spheres were treated with 5% sulfuric acid (5 volumes conc. $H_2SO_4$ and 95 volumes of $H_2O$). The compressive strengths and working times are shown in Table II.

TABLE II

Treatment - 5 Minutes in 5% $H_2SO_4$

| Ag—Cu Eutectic | Lathe Cut Alloy | Working Time | 1 Hr. Sc. |
|---|---|---|---|
| 20% | 80% | 3¾ min. | 20,900 psi. |
| 33⅓% | 66⅔% | 3½ min. | 34,560 psi. |
| 40% | 60% | 3¼ min. | 32,400 psi. |
| 50% | 50% | 1½ min. | — |

EXAMPLE 4

Following the procedure in Example 1, mechanical blends of two-thirds parts by weight of lathe cut dental amalgam alloy particles and one-third part by weight of silver-copper eutectic spheres were treated with various mineral acids and methyl alcohol solutions. The compressive strengths and working times are shown in Table III.

TABLE III

Acid & Alcohol Solutions
5 Minute Treatment

| $H_2O$ | HCl | Working Time | 1 Hr. Compressive Strength |
|---|---|---|---|
| 95 | 5 | 4½ min. | 31,360 psi. |
| 90 | 10 | 4 min. | 31,750 psi. |
| 50 | 50 | 3¾ min. | 31,000 psi. |
| — | 100 | 2¾ min. | 31,100 psi. |

| $H_2O$ | $H_2SO_4$ | Working Time | 1 Hr. Compressive Strength |
|---|---|---|---|
| 95 | 5 | 3½ min. | 34,560 psi. |
| 90 | 10 | 3½ min. | 34,050 psi. |
| 50 | 50 | 2½ min. | 32,770 psi. |
| — | 100 | — | — |

| $H_2O$ | $HNO_3$ | Working Time | 1 Hr. Compressive Strength |
|---|---|---|---|
| 95 | 5 | 4 min. | 27,400 psi. |
| 90 | 10 | 3½ min. | 30,200 psi. |
| 50 | 50 | — | — |

| $H_2O$ | METOH | Working Time | 1 Hr. Compressive Strength |
|---|---|---|---|
| 95 | 5 | 3 min. | 19,200 psi. |
| 90 | 10 | 3½ min. | 23,800 psi. |
| 50 | 50 | 3½ min. | 22,400 psi. |

TABLE III-continued

| Acid & Alcohol Solutions 5 Minute Treatment | | | |
| --- | --- | --- | --- |
| — | 100 | 3½ min. | 21,500 psi. |

NOTE:
Eutectic Concentration at 33⅓%.

I claim:

1. In a process for making a dental alloy mixture which will amalgamate to form a restoration with superior compressive strength and low creep properties by mechanically mixing lathe cut dental amalgam alloy particles and silver-copper alloy spheres, the improvement comprising treating a mechanical mixture of lathe cut dental amalgam alloy particles of minus 200 mesh, having the composition: silver 40—75%, tin 20—30%; copper 2—30%, and from 0 to 30% of one or more metals selected from the group consisting of indium, zinc, gold, mercury, manganese, cadmium and aluminum, and spheroidal silver-copper alloy of minus 325 mesh, having the composition: silver 54—72%; copper 24—40%, and varying amounts of one or more metals selected from the group consisting of nickel, zinc, tin or indium, the said mixture of alloys containing from about 20 to 50% by weight of the silver-copper alloy, with an effective amount of a treating solution selected from the group consisting of 5 volume % to 100 volume % hydrochloric acid, 5 volume % to 50 volume % sulfuric acid, 5 volume % to 20 volume % nitric acid and 5 volume % to 100 volume % methyl alcohol to aglommerate the mixture of alloy particles, separating the aglommerated mixture of alloy particles from the treating solution, washing the agglommerated alloy particles with water to remove the treating solution when the treating solution is one of the mineral acids, and finally drying the aglommerated mixture of alloy particles.

2. The process of claim 1 in which the treating solution is 10 volume % hydrochloric acid.

3. The process of claim 1 in which the effective amount of treating solution is within the range of 1 to 5 cc. of treating solution per gram of alloy mixture.

4. The process of claim 1 in which the concentration of the spheroidal silver-copper alloy in the mechanical mixture of alloys is one-third part by weight and the concentration of the lathe cut dental amalgam alloy is two-thirds parts be weight.

5. The process of claim 1 in which the spheroidal silver-copper alloy has the composition 72% weight silver and 28% weight copper.

6. The process of claim 1 in which the particle size of the lathe cut dental amalgam alloy is minus 400 mesh.

7. The process of claim 1 in which the composition of the lathe cut dental amalgam alloy is silver—70%, tin—25%, copper—3.5% and zinc—1.5%, all percentages by weight.

8. The process of claim 1 in which the spheroidal silver-copper alloy is minus 400 mesh size.

9. The dental amalgam prepared by triturating the dental alloy mixture of claim 1, which, after amalgamation, has a one-hour compressive strength of about 31,500 to 34,500 pounds per square inch, and a static creep of about 0.15%.

* * * * *